United States Patent [19]

Hermes et al.

[11] Patent Number: 5,349,047
[45] Date of Patent: * Sep. 20, 1994

[54] POLYESTERS HAVING PREDETERMINED MONOMERIC SEQUENCE

[75] Inventors: Matthew E. Hermes, Steamboat Springs, Colo.; Bin Huang, Laramie, Wyo.

[73] Assignee: United States Surgical Corporation, Norwalk, Conn.

[*] Notice: The portion of the term of this patent subsequent to Sep. 28, 2010 has been disclaimed.

[21] Appl. No.: 75,692

[22] Filed: Jun. 16, 1993

Related U.S. Application Data

[60] Division of Ser. No. 914,179, Jul. 14, 1992, Pat. No. 5,256,762, and a continuation-in-part of Ser. No. 914,179, Jul. 14, 1992, Pat. No. 5,256,762.

[51] Int. Cl.⁵ .............................................. C08G 69/00
[52] U.S. Cl. ................................... 528/361; 528/271; 528/357; 606/228; 606/230
[58] Field of Search ........................ 528/44, 45, 68, 70, 528/74, 85, 86, 271, 310, 332, 350, 354, 357, 361, 363; 606/228, 230

[56] References Cited

U.S. PATENT DOCUMENTS

| | | |
|---|---|---|
| 3,773,737 | 11/1973 | Goodman et al. |
| 3,960,152 | 6/1976 | Augurt et al. |
| 4,243,775 | 1/1981 | Rosensaft et al. |
| 4,441,496 | 4/1984 | Shalaby et al. |
| 4,481,353 | 11/1984 | Nyilas et al. |
| 4,737,550 | 4/1988 | Tomalia et al. ............... 528/363 |
| 4,857,599 | 8/1989 | Tomalia et al. ............... 528/363 |
| 4,916,193 | 4/1990 | Tang et al. ............... 528/354 |
| 4,916,209 | 4/1990 | Fung et al. |
| 4,920,203 | 4/1990 | Tang et al. ............... 528/354 |
| 4,994,551 | 2/1991 | Fung et al. |
| 5,030,703 | 7/1991 | Pielartzik et al. ............... 528/176 |
| 5,041,516 | 8/1991 | Frechet et al. ............... 528/363 |
| 5,066,772 | 11/1991 | Tang et al. ............... 528/354 |
| 5,120,802 | 6/1992 | Mares et al. ............... 528/354 |
| 5,145,945 | 9/1992 | Tang et al. ............... 528/354 |
| 5,152,781 | 10/1992 | Tang et al. ............... 528/354 |

FOREIGN PATENT DOCUMENTS

0359038 3/1990 European Pat. Off. .
WO89/05664 6/1989 PCT Int'l Appl. .

OTHER PUBLICATIONS

Goodman et al., Polydepsipeptides I. Synthesis and Characterization of Copolymers of $\alpha$-Amino and $\alpha$-Hydroxy Acids, Israel Journal of Chemistry, vol. 10, pp. 867–879 (1972).
Goodman et al., Polydepsipeptides II: Synthesis and Preliminary Conformational Studies of an Alternating $\alpha$-Amino and $\alpha$-Hydroxy Acid Polymer, Israel Journal of Chemistry, vol. 12, Nos. 1–2, pp. 67–77 (1974).
Ingwall et al., Polydepsipeptides. III. Theoretical Conformational Analysis of Randomly Coiling and Ordered Depsipeptide Chains, Macromolecules, vol. 7, No. 5, pp. 598–605 (1974).
Ingwall et al., Polydepsipeptides. 5. Experimental Conformational analysis of Poly(L-alanyl-L-Lactic acid) and Related Model Compounds, Macromolecules vol. 9, No. 5, pp. 802–808 (1976).
Mathias et al., Polydepsipeptides. 6. Synthesis of Sequential Polymers Containing Varying Ratios of L-Alanine and L-Lactic Acid, Macromolecules, vol. 11, No. 3, pp. 534–539 (1978).
Goodman, Matrix-Controlled Synthesis and Conformational Studies of Polydepsipeptides, Journal of Polymer Science: Polymer Symposium 62, 173–188 (1978).
Zhang et al., Nanoarchitectures. 1. Controlled Synthesis of Phenylacetylene Sequences, J. Am. Chem. Soc. 114, pp. 2273–2274 (1992).

*Primary Examiner*—John Kight, III
*Assistant Examiner*—Shelley A. Dodson

[57] ABSTRACT

Polyesters having predetermined monomeric sequence are produced by stepwise addition of monomeric hydroxyacids to a growing polymeric chain. Included herein are various polyesters having predetermined primary sequence, various methods of producing polyesters having predetermined primary sequence, various articles formed from polyesters having predetermined primary sequence and various methods of using such articles.

29 Claims, 1 Drawing Sheet

FIG. 1

POLYESTERS HAVING PREDETERMINED MONOMERIC SEQUENCE

This application is a divisional continuation-in-part of U.S. patent application Ser. No. 07/914,179, filed Jul. 14, 1992 now U.S. Pat. No. 5,256,762 the contents of which are incorporated herein by reference.

BACKGROUND OF THE INVENTION

1. Field of the Invention

The present invention relates to polyesters having predetermined monomeric sequence, i.e., they are exactly sequenced polyesters, and to methods of producing such exactly sequenced polyesters, and various articles produced from such exactly sequenced polyesters. More particularly, homogeneous hydroxyacid polymers having precisely defined sequences are produced according to the present invention.

2. Description of Related Art

Hydrolyzable polyesters such as those derived from polyhydroxyacids have many important applications as biodegradable polymers. The simplest poly($\alpha$-hydroxyacid), polyglycolic acid has been successfully used as a bioabsorbable implant material in surgical procedures. Likewise, polylactic acid has been used as a bioabsorbable implant material, either by itself or as a copolymer with glycolic acid. Other hydroxyacids, e.g., hydroxybutyric acid have also been utilized.

Polyglycolic acid is generally prepared from the cyclic diester of glycolic acid (glycolide) by ring opening addition polymerization in the presence of a catalyst. In a similar manner, polylactic acid can be obtained from the cyclic diester of lactic acid (lactide) by stannous octoate-catalyzed ring opening polymerization.

Copolymers of glycolic acid and lactic acid have been developed in an attempt to combine the characteristics of both compounds and extend the range of polymer properties and rates of hydrolysis. For example poly-L-lactic acid is hydrolyzed more slowly than polyglycolic acid and copolymers of the two acids can be made to hydrolyze at intermediate rates.

Poly(lactide-co-glycolide) polymers are heterogeneous, i.e., they are made up of a random sequence of lactate and glycolate dimers and it is statistically improbable any two chains will be identical. Ordinarily, properties of such copolymers are based, in part, upon the concentration of lactide and glycolide present in the starting reaction mixture. The formation of the copolymer is complicated by the fact that depending upon the catalyst used and other reaction conditions, the relative rates of reactivity of glycolide and lactide are different. For example, when equimolar amounts of glycolide and lactide are reacted, glycolide is initially more likely to combine with growing chains than is lactide. Consequently, the initial composition of the growing chain contains a predominance of glycolic acid units occasionally and randomly interspersed with short sequences of lactic acid units. As the reaction proceeds, the concentration of lactide contained in the mixture increases relative to glycolide and the ratio of glycolic acid units to lactic acid units forming the chain becomes more equal. As the reaction nears completion, most available glycolide has polymerized and the relative amount of lactide is high. Consequently, a larger number of lactic acid units are likely to come together and polymerize. Thus, the first portion of the copolymer chain is likely to contain a predominance of glycolic acid units, and the end portion of the chain is likely to contain a predominance of lactic acid units.

Random sequences generated by the synthesis of poly(lactide-co-glycolide) result in the formation of heterogeneous polymers, i.e., no two polymeric chains are likely to be identically duplicated. Consequently, the physical and chemical properties of such copolymers are difficult to predict or control with a high degree of precision. The ability to control synthesis of the precise compositional sequence of poly(lactide-co-glycolide) polymers would allow the physical and chemical properties of the polymeric products to be fixed to a high degree of certainty and allow the production of homogeneous polymers. For example, such control would allow polymers to be engineered to more precisely fit specific specifications such as degree of crystallinity and/or rates of hydrolysis.

It has been reported that pure polyglycolide is about 50% crystalline and pure poly-L-lactide is about 37% crystalline. See Gilding et al., Biodegradable Polymers for Use in Surgery, Polymer, 20:1459–1464 (1979). Gilding et al. also reported that poly(lactide-co-glycolide) polymers are amorphous between the compositional range of from 25 to 75 mole percent glycolide. This is so because of the amorphous character of the copolymer. For crystallinity to occur, extensive lengths of the chain need steric regularity which may be achieved with precise sequence control.

Precise control over the sequential arrangement of poly(lactide-co-glycolide) also would allow control over the rate of hydrolysis of the copolymer. The rate of hydrolysis of a glycolic acid-glycolic bond is greater than the rate of hydrolysis of lactic acid-glycolic acid bond which is greater than the rate of hydrolysis of a glycolic acid-lactic acid bond which is greater than the rate of hydrolysis of a lactic acid-lactic acid bond. Thus, in the copolymer segment:

wherein glycolide is oriented to provide a hydroxy terminus on the left-most portion of the segment, i.e., HOCH$_2$CO$_2$CH$_2$ . . . COOH, the order of hydrolysis is 1>4>2>3, i.e., 1 is fastest and 3 is slowest. Therefore, an engineered arrangement of sequential units would allow control over the rate at which a copolymer hydrolyzes.

U.S. Pat. No. 3,960,152 (the "'152 patent") describes an attempt to provide a copolymer having a controlled sequence of alternating units of lactic acid and polyglycolic acid. According to the '152 patent, lactic acid and glycolic acid are formed into a cyclic diester (3-methyl-1,4-dioxane-2,5-dione). When the cyclic diester is opened and added to a polymer chain, the lactic acid unit and glycolic acid unit are said to be adjacent in the polymer chain. However, there is no way to control the ring opening polymerization such that the ring opens at the same position every time. Thus, the ring opening and subsequent addition cannot be strictly uniform and the final product does not contain regularly alternating lactic acid units and glycolic acid units, i.e., the resulting polymer is not homogeneous.

Polydepsipeptides are copolymers of $\alpha$-amino and $\alpha$-hydroxycarboxylic acids with neighboring monomers linked either by an amide or an ester bond. Such copolymers are described as appropriate models for the conformational and optical properties of polypeptides and proteins. See, e.g., Goodman et al., Polydepsipeptides II: Synthesis and Preliminary Conformational Studies of an Alternating α Amino and Hydroxy Acid Polymer, Israel Journal of Chemistry, 12:66–77 (1974) or Mathias et al., Polydepsipeptides.6. Synthesis of Sequential Polymers Containing Varying Ratios of L-Alanine and L-Lactic Acid, Macromolecules, 11 No. 3: 534–539 (May-June 1978). In these references, no more than two adjacent lactic acid residues were esterified with alanine to form polydepsipeptides for the purpose of allowing qualitative evaluation of the helix disrupting ability of two adjacent lactic acid residues.

Therefore, it would be advantageous to construct a polyester having a predetermined sequence of structural units by controlling the precise sequential arrangement of monomers in a polyester chain.

SUMMARY OF THE INVENTION

The present invention involves polyesters having a predetermined monomeric sequence. Such polyesters are produced by the stepwise addition of monomeric units to a growing polymeric chain. Hydroxyacids such as glycolic acid, lactic acid and hydroxybutyric acid are esterified to form carefully regulated sequences. The resulting sequential polyesters have precisely engineered sequential arrangements which allow control over their molecular weight, rates of hydrolysis, crystallinity and other associated chemical and physical properties.

Preparation of sequential polyesters according to the present invention may be commenced by blocking or protecting the hydroxyl group of a first hydroxyacid. Dimer formation is accomplished by activating the carboxyl terminus of the first hydroxyacid so that esterification with a second optionally carboxyl-protected hydroxyacid occurs. If protected, the carboxyl group of the second hydroxyacid is deprotected to allow subsequent addition of a third carboxyl-protected hydroxyacid. Stepwise addition of further optionally carboxyl protected hydroxyacids allows the sequence of the resulting homogeneous polymer to grow and be carefully regulated.

Polyesters having predetermined monomeric sequence can also be manufactured by reacting an optionally carboxyl-protected hydroxyacid with a hydroxy acid containing at least one carboxyl group. After esterification, the carboxyl group of a carboxyl-protected hydroxyacid is deprotected to allow subsequent stepwise addition of further optionally carboxy-protected hydroxyacids. Branched polyesters such as dendritic polymers can be manufactured by incorporation of hydroxy polycarboxylic acids into a growing polyester having predetermined monomeric sequence.

Polyesters having predetermined monomeric sequences can also be made by solid phase synthesis. The carboxyl group of a first hydroxyacid is covalently bonded to a resin support to allow addition of a second hydroxy-protected hydroxyacid. To allow subsequent addition of a third hydroxy-protected hydroxyacid, the hydroxyl group on the second hydroxyacid must be deprotected. Stepwise addition of further hydroxyl-protected hydroxyacids in the same manner allows the sequence to grow and be carefully regulated. Solid phase sequential polyester synthesis is amenable to automation.

The present invention provides exactly sequenced polyesters, methods of synthesizing exactly sequenced polyesters, various articles formed from exactly sequenced polyesters and methods of using such articles.

DETAILED DESCRIPTION OF THE INVENTION

Polyesters having predetermined monomeric sequence according to the present invention are those polyesters having a precise sequential monomeric order. The ability to engineer the precise chain sequence and length permits regulation of chemical and physical properties such as crystallinity, rates of hydrolysis and molecular weight of resulting polymers. As used herein, the terms "polyester having predetermined monomeric sequence" and "sequential polyesters" are equivalent and are used interchangeably.

Generally speaking, sequential polyesters in accordance with the present invention are made by placing protecting groups on all available reactive sites except those necessary to form the desired ester bond between successive monomers. In this manner the sequential arrangement of the polymers is carefully regulated by stepwise addition of predetermined monomeric units. The common available reactive sites of a hydroxyacid molecule are the carboxyl group and the hydroxyl group. Successive selective protection, deprotection and formation of a bond between hydroxyacid molecules form the basis of the invention herein.

Hydroxyacids which are useful according to the present invention may be represented by the formula R-COOH wherein R contains one or more hydroxyl groups and/or one or more carboxyl groups and is an essentially hydrocarbonaceous moiety. By the phrase "essentially hydrocarbonaceous", it is meant that R may contain hetero atoms provided they do not inhibit polymerization to an unacceptable degree. If the homogeneous sequential polyester is meant to be hydrolyzable, such hetero atoms do not inhibit degradation of the polymer to an unacceptable degree. If the homogeneous sequential polyester is meant to be implantable, such hetero atoms do not give rise to toxic degradation products which may be difficult to metabolize.

Suitable hydroxyacids include α-hydroxyacids such as glycolic acid ("G"), lactic acid ("L"), and α-hydroxyisobutyric acid ("αHB"); β-hydroxyacids such as β-hydroxybutyric acid ("βHB"); and γ-hydroxyacids such as γ-hydroxyvaleric acid ("γHV"). Preferred hydroxyacids in accordance with the present invention are α-hydroxyacids while the most preferred hydroxyacids are glycolic acid and lactic acid. It should be understood that these examples are merely illustrative and that any hydroxyacid capable of esterification is within the scope of the present invention.

Polyesters having predetermined monomeric sequence include sequential combinations of all the above-noted hydroxyacids. Thus, a sequential polyester can be constructed with one, two, three, four or more different hydroxyacids bonded together in a predetermined order. For example, a polyester can include the sequence G-G-L-L-αHB-αHB-HV-HV or G-L-αHB-HV-G-L-αHB-HV or any conceivable combination of the various hydroxyacids described above.

In synthesizing exactly sequenced polyesters, the hydroxyl group(s) of a first hydroxyacid is protected by a suitable hydroxyl protecting group. Such hydroxyl protecting groups and methods of protection are described in "Protective Groups in Organic Synthesis" by Theodora W. Green, John Wiley & Sons, N.Y., 1981 whose contents are incorporated herein by reference. Hydroxyl group protection can occur, e.g., by formation of methoxymethyl ethers, t-butoxymethyl ethers, methoxyethoxymethyl ethers, bis(2-chloroethoxy)-methyl ethers, 2-(trimethylsilyl)ethoxymethyl ethers, tetrahydropyranyl ethers, 4-methoxytetrahydropyranyl ethers, tetrahydrofuranyl ethers, 1-ethoxyethylethers, 1-methyl-1-methoxyethyl ethers, 1-(isopropoxy)ethyl ethers, trimethylsilyl ethers, triethylsilyl ethers, t-butyl-dimethylsilyl ethers, formate esters, benzyl formate esters, chloroacetate esters, dichloroacetate esters and other selected esters.

Any hydroxyl protecting group is suitable for practicing the method disclosed herein as long as protection and/or deprotection is accomplished in such a manner as to not adversely effect formation of the polyester chain. Thus, removal of the protective group should not lead to destruction of the polyester or the production of side products that would interfere with the overall process. Various methods of deprotecting the aforesaid hydroxyl groups are known by those with skill in the art and described, e.g., by Green in the above noted reference.

Preferred hydroxyl protecting groups according to the present invention form methoxyethoxymethyl ethers, tetrahydropyranyl ethers, 1-ethoxy-ethyl ethers and 1-methyl-1-methoxyethyl ethers, while the most preferred hydroxyl protecting groups form tetrahydropyranyl ethers or methoxy ethoxyethyl ethers.

In one aspect, aliphatic esters of hydroxy acids are preferred starting materials according to the present invention. For example, as is discussed below, methyl glycolate, ethyl glycolate, propyl glycolate, methyl lactate, ethyl lactate, propyl lactate, etc. may be hydroxyl-protected and then subjected to hydrolysis to remove the aliphatic moiety during synthesis of sequential polyesters.

A second hydroxyacid, which may be the same or different than the first hydroxyacid, is reacted with the first hydroxyacid to form the first ester bond. In one embodiment, the reactivity of the carboxyl group of the second hydroxyacid may be suppressed to accomplish such esterification. In an alternative embodiment, the carboxyl group of the hydroxyacid is not blocked and remains a free acid. When the carboxyl group is blocked, only the hydroxyl group of the second hydroxyacid is available to react with the carboxyl group of the first hydroxyacid. The carboxyl group of the second hydroxyacid may be masked by ester formation, e.g., methyl, ethyl and benzyl ester derivatives. Any carboxyl protecting group is suitable for practicing the method disclosed herein as long as protection and/or deprotection is accomplished in such a manner as to not effect formation of the polyester chain. Thus, removal of the protective group should not lead to destruction of the polyester or the production of side products that would interfere with the overall process. The most preferred carboxyl protecting groups are benzyl esters.

The hydroxyl-protected first hydroxyacid is then reacted with the second carboxyl-protected hydroxyacid in the presence of a dehydrating agent and solvent to yield a dimer ester. Suitable solvents are well-known in the art, e.g., see Mathias et al. supra. Examples of useful dehydrating agents which promote esterification include dicyclohexylcarbodiimide (DCDI), trifluoroacetic anhydride, and N,N'-carbonyldiimidazole (CDI). The preferred dehydrating agent is DCDI.

As was stated above, esterification may proceed without blocking the carboxyl group of the second hydroxyacid when DCDI is used as the dehydrating agent. The reaction may be illustrated as follows:

ester + dicycohexylurea

A third hydroxyacid, which may be the same or different than either the first or second hydroxyacid, is then reacted with the second hydroxyacid to form a trimer. As with the second hydroxyacid, the carboxyl group of the third hydroxyacid may optionally be masked prior to reaction with the second hydroxyacid. Any protecting group which masks the carboxyl group on the second hydroxyacid must be removed before the reaction can proceed. Such removal is accomplished by means which are known to those with skill in the art. For example, a benzyl ester is removed by exposure to $H_2$ and Pd to yield the free acid. As above, formation of the ester bond between the second and third hydroxyacids is promoted by a dehydrating agent.

In accordance with the present invention, successive hydroxyacids can be added as described above to form tetramers, pentamers etc. In this manner, the controlled addition of selected hydroxyacids yields polymer chains having precisely defined monomeric sequences. The reaction sequence is illustrated below in relation to α-hydroxyacids and formation of a trimer. As used below, $R^1$, $R^2$ and $R^3$ may be the same or different and are essentially hydrocarbonaceous.

When the polymer has reached a predetermined length and no further additions are desired, the hydroxyl protecting group on the first hydroxyacid is removed by such methods as are known to those with skill in the art. For example, mild acid hydrolysis can be used to remove a vinyl ether protecting group. Likewise, any carboxyl protecting group may be removed from the final hydroxyacid by methods that are known to those with skill in the art, e.g., $H_2$, Pd. The polymer is then ready to undergo further processing and be formed into a desired shape.

In an alternative embodiment of the present invention, a polyester having a predetermined monomeric sequence can be synthesized by starting with a carboxylic acid such as acetic acid. In this manner, a first carboxy-protected hydroxyacid such as an α hydroxyacid is reacted with a carboxylic acid in the presence of a dehydrating agent to form a dimer having an ester bond. For example:

wherein R' and $R^1$ may be the same or different and are essentially hydrocarbonaceous. Formation of an oligomer by addition of successive hydroxyacids is accomplished as described above, e.g., by successive protection/deprotection and ester bond formation until a polymer of desired length is obtained. As was also discussed above, esterification may proceed without blocking the carboxyl groups of subsequently added hydroxyacids by isolating the hydroxyacid-DCDI complex and reacting the isolate with a subsequent hydroxyacid.

Polycarboxylic acids may also be utilized to begin formation of polyesters having predetermined monomeric sequence. Thus, a polycarboxylic acid such as a dicarboxylic acid is reacted with a first optionally carboxy-protected hydroxyacid in the presence of a dehydrating agent to form a polyester. Such dicarboxylic acids may be aliphatic or aromatic and include, e.g., oxalic acid, malonic acid, succinic acid, glutaric acid, adipic acid and terephthalic acid.

When a dicarboxylic acid is used as starting material the resulting chain grows in two directions emanating from the initial dicarboxylic acid. For example:

Engineering, Vol. 12, pp. 811–858 (1988), whose contents are incorporated herein by reference. Such techniques are adaptable to synthesis of sequential polyesters in accordance with the present invention.

The hydroxyl group of the first hydroxyacid is masked with protecting groups as above, i.e., as described in "Protective Groups in Organic Synthesis" by Theodora W. Green, John Wiley & Sons, N.Y., 1981 supra. Preferred protecting groups according to the present invention form methoxyethoxymethyl ethers, tetrahydropyranyl ethers, 1-ethoxy-ethyl ethers and 1-methyl-1-methoxyethyl ethers, while the most prewherein R' R$^1$ and R$^2$ may be the same or different and are essentially hydrocarbonaceous and n may be zero or greater.

As above, esterification starting with polycarboxylic acids may proceed without blocking the carboxyl groups of subsequently added hydroxyacids by isolating resulting DCDI complexes and reacting the isolate with subsequent hydroxyacids.

Utilization of polycarboxylic acids having more than two carboxylic acids, e.g., citric acid is also contemplated by the present invention. In this manner, multiple chains emanate from the initial polycarboxylic acid. In the case of citric acid, three chains begin at each of the three carboxyl groups to form branched chain polymers.

In accordance with another aspect of the present invention, polyesters having predetermined monomeric sequence may be formed by automated solid phase synthesis. Solid phase sequential polyester synthesis is based upon the covalent attachment of a growing ester chain to an insoluble polymeric support or resin carrier so that unreacted reagents can be removed by filtration or washing. After the chain has been established, the sequential polyester is removed from the support under conditions which do not adversely effect the polyester.

To accomplish solid phase sequential polyester synthesis, the carboxyl group of a first hydroxyacid is covalently bonded to an insoluble resin support via a bifunctional spacer. The insoluble support is functionalized with a functionalizer such as chloromethyl, aminomethyl or benzhydrylamino groups. One end of the bifunctional spacer reacts with the resin bound functionalizer and the other end reacts with the free carboxyl group of a hydroxyl-protected hydroxyacid to form a covalently bonded hydroxyacid/polymer complex.

The resin support may be a polystyrene suspension polymer cross-linked with 1% of M-divinylbenzene. Solid phase synthesis is known in relation to synthesizing sequential peptides. An overview of techniques and materials used in solid phase peptide synthesis is provided in the Encyclopedia of Polymer Science and ferred hydroxyl protecting groups form tetrahydropyranyl ethers or methoxyethoxymethyl ethers.

The free carboxyl group of the first hydroxy acid is then covalently bonded to the resin support. A second hydroxyacid which may be the same or different than the first hydroxyacid is then reacted with the first hydroxyacid in the presence of a dehydrating agent to form an ester bond and begin chain formation. In order to accomplish such esterification, the hydroxyl-protecting group must be removed from the first hydroxyacid in the manner described above, thus leaving the hydroxyl group free to react with the free carboxyl group of the second hydroxyacid. The hydroxyl group of the second hydroxyacid must be masked, as above, in order for the reaction to proceed without formation of unwanted side chains.

Successive hydroxyacid molecules may then be added in stepwise fashion. For example, a trimer may be formed by adding a third hydroxyacid, which may be the same or different than either the first or second hydroxyacid, to the growing chain. In solid phase sequential polyester synthesis according to the present invention, the hydroxyl group of each successive hydroxyacid must be masked to allow the formation of precisely engineered homogeneous sequential polyesters. Before the third or more hydroxyacids are sequentially added, the hydroxyl group of each previously esterified hydroxyacid must be deprotected to allow ester bond formation with the next hydroxyacid. Deprotection of masked hydroxyl groups may be accomplished as described above.

When a sequential polyester chain reaches the desired length, the polyester is cleaved from the resin support and the final hydroxyl protecting group is removed. The bifunctional spacer should incorporate a smoothly cleavable protecting group on the end which bonds to the hydroxyacid. Suitable bifunctional spacers are well-known in the art. Cleavage reagents are known and include acids and nucleophiles.

Dendritic polymers may be manufactured in accordance with the present invention by incorporation of hydroxy polycarboxylic acids into a growing polyester chain. Examples of such hydroxy polycarboxylic acids include Tartronic acid, malic acid, citric acid, etc. Accordingly, a polyester having predetermined monomeric sequence is made in any manner disclosed above and, at a predetermined point in the growing chain, a hydroxy polycarboxylic acid is incorporated. Subsequent hydroxyacids then form branched chains which emanate from the carboxyl groups of the polycarboxylic acid. If further branching is desired, any number of additional hydroxy polycarboxylic acids may be incorporated at any point in the branched chain to create further branching. For example:

more quickly than the central portion of the copolymer chain.

In accordance with the present invention, thermoplastic elastomers may be constructed. Thermoplastic elastomers are multiphase compositions in which the phases are intimately dispersed. The present invention allows thermoplastic elastomers to be constructed by sequential addition of appropriate monomers to form hard and soft segments within the polymer.

Sequential polyesters according to the present invention also allow more crystalline structures to be produced. Extensive control over the chain sequence allows steric regularity to be achieved. Thus, while prior wherein X is a portion of a polyester having predetermined monomeric sequence according to the present invention and $R^1$ is essentially hydrocarbonaceous.

As above, dendritic esterification may proceed without blocking the carboxyl groups of subsequently added hydroxyacids or hydroxy polycarboxylic acids by isolating resulting DCDI complexes and reacting the isolate with subsequent hydroxyacids or hydroxy polycarboxylic acids.

Polyesters having predetermined monomeric sequence made in accordance with the present invention are suitable for use in a variety of applications. By varying the sequence and length of the polymer, the physical and chemical properties of the polymers can be engineered to meet predefined specifications.

The speed with which a sequential polyester degrades in an environment is based, in part, upon the rate of hydrolysis of ester bonds in the polymer chain. The present invention allows the rate of hydrolysis to be tailored in predictable fashion based upon sequence. Indeed, the exacting nature of the copolymers allows the rate of hydrolysis to be more predictable than prior random copolymers. If desired, the end portions of a sequential copolymer may be engineered to hydrolyze poly(lactide-co-glycolide) polymers containing 25 to 75 mole percent glycolide are amorphous, copolymers containing between 25 to 75 mole percent glycolide can be made crystalline. In this manner, the tensile strength and other physical properties can be regulated to a high degree, i.e., by varying the proportion of crystalline region to amorphous region, properties such as tensile strength and brittleness may be varied to suit particular applications.

In accordance with the present invention, oligomers of sequential polyesters may be coupled to prepare larger, higher molecular weight chains of sequential polyesters. In one aspect, hydroxyl protected hydroxyacid molecules are combined with carboxyl protected hydroxyacid molecules and esterified to yield a bulk solution containing dimers which are both hydroxy-protected and carboxy-protected. The bulk solution is split into two portions: the first is then hydroxyl-deprotected and the second is then carboxyl deprotected. The two portions are then combined in the presence of dehydrating agent to yield tetramers in large quantity. The process maybe continued until polymers of desired length are obtained. For example, coupling of methoxyethoxymethyl-protected glycolic acid (MEM-G) and benzyl lactate (L-benzyl) using DCDI gives the MEM-G-L-Benzyl dimer in high yield. The dimer is then separated into two substantially equal portions. The MEM protecting groups are removed from one portion to yield free hydroxyl groups and the benzyl protecting groups are removed from the other portion to yield free acid groups. The two portions are then combined in the presence of DCDI to give MEM-G-L-G-L-Benzyl in bulk quantities. This product is then split into two portions, the MEM protecting group removed from one portion and the benzyl protecting group removed from the other portion. The two portions are then combined in the presence of DCDI to give MEM-G-L-G-L-G-L-G-L-Benzyl in bulk quantities. The splitting/deprotecting/combining/coupling procedure is repeated until bulk quantities of polymer chains of desired length are achieved. The only limitation on the size or molecular weight of polymers so formed is the solubility of the polymer in the solvent. In accordance with the present invention, sequential polymers may have low molecular weights, e.g., the dimeric species to high molecular weights, e.g., about 20,000–50,000 or greater.

Alternatively, oligomers of sequential polyesters may be coupled to prepare larger, higher molecular weight chains of sequential polyesters by bulk polymerization of pentachlorophenol ester monomers. An inert matrix such as Celite TM diatomaceous earth may be used to enhance removal of the pentachlorophenol during thermal polymerization in vacuum and lead to higher yields and molecular weights. A p-nitrophenol ester may also be used to promote bulk polymerization.

The polyesters having predetermined monomeric sequence produced in accordance with the present invention may be combined to form block copolymers having highly uniform characteristics. Methods of forming block copolymers are well known in the art.

Useful products made from sequential polyesters include fibrous surgical articles such as sutures, prosthetic ligaments, prosthetic tendons, woven mesh, gauze, dressings, growth matrices and the like. Such fibrous surgical articles may be engineered to be made more or less elastic depending upon end use. Portions of a single length of monofilament can be made to hydrolyze at different rates and to be more or less elastic than other portions.

Figure 1:
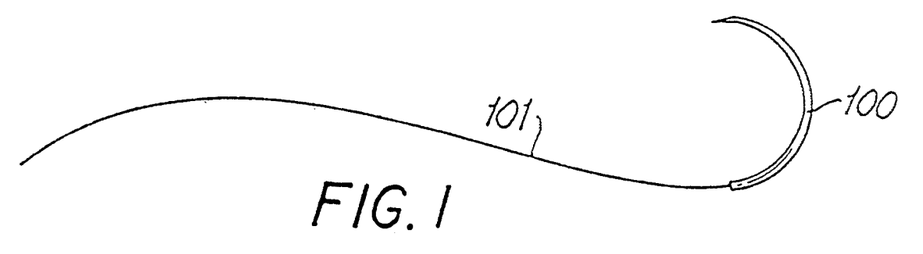
FIG. 1 is a depiction of a suture and needle combination.

A suture in accordance with the present invention, suture 101, may be attached to a surgical needle 100 as shown in FIG. 1 by methods well known in the art. Wounds may be sutured by passing the needle suture through tissue to create a wound closure. The needle preferably is then removed from the suture and the suture is tied.

Other medical articles can be manufactured from the sequential polyesters of the present invention. These include, but are not limited to, staples, clips and other fasteners, drug delivery devices, pins, screws and other implants. Implantable surgical articles made from the polyesters of this invention may be designed to be implanted into patients where the articles are hydrolyzed and absorbed.

Drug delivery devices, as used herein, include any device or article of manufacture which is used to deliver a medicinal agent. The term "medicinal agent" is used in its broadest sense and includes any substance or mixture of substances which are useful in medicine. Thus, it is understood that a medicinal agent may be a drug, enzyme, peptide, protein, dye, or diagnostic agent such as a releasable dye which may have no biological activity per se.

Examples of various of medicinals that can be used in accordance with the present invention include antimicrobials, analgesics, antipyretics, anesthetics, antiepileptics, antihistamines, anti-inflammatories, cardiovascular drugs, diagnostic agents, sympathomimetics, cholinomimetics, anti-muscarinics, antispasmodics, hormones, growth factors, muscle relaxants, adrenergic neuron blockers, anti-neoplastics, immunosuppressants, gastrointestinal drugs, diuretics, steroids and enzymes. It is also intended that combinations of medicinals can be used in accordance with the present invention.

Sequential polyesters are well-suited for use as biodegradable polymers that are being used to address environmental concerns. For example, disposable staple items constructed from hydrolyzable sequential polyesters would biodegrade in landfills or in the ocean without leaving any toxic or non-degradable residue.

EXAMPLE 1

Construction of Carboxyl Protected Hydroxyacid

Construction of Benzyl-L-lactic Acid. L-Lactic acid (9 g, 100 mmol) is added to N,N'-diisopropylbenzylisourea (23.3 g, 100 mmol) with stirring. The mixture becomes very viscous within 10 min and is stirred intermittently for 1 h. The volume is then increased to 200 mL with THF, and the mixture stirred for 48 h at room temperature. After cooling the mixture to −15° C., the diisopropylurea is removed by filtration and the THF is evaporated under reduced pressure. The resulting thick oil is pumped under high vacuum for 24 h to give benzyl lactate (17.4 g, 95%) which may be used without further purification.

EXAMPLE 2

Construction of Carboxyl Protected Hydroxyacid

Construction of Benzyl-glycolic Acid. Glycolic acid (5.89,100 mmol) is added to N,N'-diisopropylbenzylisourea (23.3 g, 100 mmol) with stirring for 1 hour. The volume is then increased to 200 M1 with THF, and the mixture stirred for 48 h at room temperature. After cooling the mixture to −15° C., the diisopropylurea is removed by filtration and the THF evaporated under reduced pressure. The resulting product is pumped under high vacuum for 24 h to give benzyl glycolate which may be used without further purification.

EXAMPLE 3

Construction of Carboxyl Protected Hydroxyacid

Construction of Benzyl Lactate. To a solution of lactic acid (Aldrich Chemical Co.) (60 g, 0.666 mole) and triethyl amine (Aldrich) (67.4 g, 0.666 mole) in acetonitrile (J. T. Baker) (60 ml), was dropwise added benzyl chloride (Mallinkrodt) (42 g, 0.333 mol) with stirring at refluxing temperature. The solution was refluxed overnight and then $CH_3CN$ was removed in vacuum. The solution was then diluted with 150 ml H20 and was extracted with 4×100 ml ethyl acetate. The organic solution was combined and washed with saturated $Na_2CO_3$ aq. solution (50 ml), 1% HCl (50 ml) and saturated NaCl aq. solution (50 ml) and dried with $MgSO_4$. The solvent was removed in vacuum and 41.0 g crude product was obtained. The crude product was vacuum fractional distilled and the fraction of above 120° C. at 120 mmHg was collected (28.0 g, yield 47.%).

$^1$HNMR (270 Mz, CDCl$_3$) δ1.44 (d, 3H, J=5.4 Hz); δ2.80 (d, 1H, J=5.4 Hz); δ 4.33 (m, 1H); δ 5.22 (s, 2H); § 7.37 (m, 5H).

EXAMPLE 4

Construction of Hydroxyl Protected Hydroxyacid

Construction of the 1-ethoxyethyl ether of lactic acid. Lactic acid (7.2 g, 100 mmol) is reacted with a two fold excess of ethyl vinyl ether in dry THF in the presence of a trace of hydrogen chloride. After 16 hrs, THF and excess ethyl vinyl ether are removed under vacuum and the 1-ethoxyethyl ether of lactic acid is recovered and used without further purification.

EXAMPLE 5

Construction of Hydroxyl Protected Hydroxyacid

Construction of the 1-ethoxyethyl ether of glycolic acid. Glycolic acid (5.8 g, 100 mmol) is reacted with a two fold excess of ethyl vinyl ether in dry THF in the presence of a trace of hydrogen chloride. After 16 hrs, THF and excess ethyl vinyl ether are removed under vacuum and the 1-ethoxyethyl ether of glycolic acid is recovered and used without further purification.

EXAMPLE 6

Construction of Hydroxyl Protected Aliphatic Ester of Hydroxyacid

Construction of methoxyethoxymethyl (MEM) protected ethyl glycolate. To a solution of MEM chloride (Aldrich Chemical Co.) (25 g, 0.2 mole) in methylene chloride (100 ml) was added dipropylethyl amine (Aldrich) (35 ml, 0.2 mole) at 0° C. with stirring, followed by addition of ethyl glycolate (Aldrich) (15 ml, 0.154 mole). The solution was allowed to stand overnight with stirring at room temperature and an orange-red color appeared. The solution was washed with 30 ml H$_2$O and the water phase was extracted with 50 ml, 30 ml methylene chloride. The organic phases were combined and washed with 50 ml saturated NaHCO$_3$ aqueous solution, 50 ml 1% HCl and 50 ml saturated NaCl aqueous solution, dried by anhydrous MgSO$_4$ and the solvent was removed in vacuum. Product (21.0 g) was obtained with yield of 71%.

EXAMPLE 7

Hydrolysis of Hydroxyl Protected Aliphatic Ester of Hydroxyacid

Hydrolysis of MEM-protected ethyl glycolate. MEM ethyl glycolate (10.0 g, 0.05203 mole) in ethanol (150 ml) was stirred with sodium hydroxide (6.8 g, 0.1705 mole) overnight. The solution was diluted with 150 ml H$_2$O and the solution was concentrated to 100 ml in vacuum. The solution was adjusted to a pH about of 7-8 by addition of HCl and then extracted with 50 ml ethyl acetate which was discarded. The water phase was adjusted to a pH 1.0 by addition of HCl and extracted with 4×50 ml ethyl acetate. The organic phase was combined and washed with 100 ml water and dried with MgSO$_4$. The solvent was removed in vacuum and the product (5.02 g) results in a yield of 59%. $^1$HNMR (270 Mz, CDCl$_3$) δ3.40 (s, 3H); δ3.58 (t, 2H, J=2.7 Hz); δ3.77 (t, 2H, J=2.7 Hz); δ4.26 (s, 2H); δ4.82 (s, 2H).

EXAMPLE 8

Construction of Dimers

Construction of MEM-G-L-Benzyl. To a solution of MEM-G (2.5 g, 0.015 mole) and L-Benzyl (1.83 g, 0.01016 mole) in acetonitrile (Aldrich) (25 ml) containing a trace amount of 4-dimethylaminopyridine (DMAP) (Aldrich) was added DCDI (Aldrich) (3.14 g, 0.015 mole) with stirring at room temperature. The solution was allowed to stand overnight with stirring at room temperature. The precipitate was filtered and the filtrate was concentrated in vacuum. The residue was diluted with 30 ml ethyl ether and filtered again to remove solid. The solvent was removed in vacuum and 4.4 g liquid product was collected. The product was applied to a column of 50 g Silica gel 60 (63–200 mm of particle size) and eluted with methylene chloride and ethyl acetate (2:1 in v/v) 3.1 g product was obtained with yield of 93.5%. $^1$H NMR (270 Mz, CDCl$_3$) δ1.52 (d, 3H, J=7.3 Hz); δ3.39 (s, 3H); δ3.55 (t, 2H, J=3.6 Hz); δ3.74 (t, 2H, J=3.6 Hz); δ4.28 (s, 2H); δ4.80 (s, 2H); δ5.18 (s, 2H); δ5.21 (q, 1H, J=7.3 Hz); δ 7.34–7.35 (m, 5H); $^{13}$C NMR (270 Mz, CDCl$_3$) d169.96 (1C); 169.44 (1C); 135.17 (1C); 128.49 (2C); 128.30 (1C); 127.99 (2C); 95.29 (1C); 71.55 (1C); 68.81 (1C); 67.29 (1C); 66.95 (1C); 63.98 (1C); 58.80 (1C); 16.72 (1C).

EXAMPLE 9

Construction of Oligomers

Construction of L-G-L-G-L-G hexamer. Ethyl carboxyethyl acetal is reacted with benzyl glycolate in the presence of dicyclohexylcarbodiimide (DCDI) to yield an acetal benzyl ester dimer. The ester group is removed by treatment with H$_2$, Pd and the dimer reacted with benzyl lactate in the presence of DCDI. The resulting trimer is treated with H$_2$, Pd and reacted with benzyl glycolate in the presence of DCDI to yield a tetramer. The tetramer is treated with H$_2$, Pd and reacted with benzyl lactate in the presence of DCDI. The resulting pentamer is subjected to H$_2$, Pd and reacted with benzyl glycolate in the presence of DCDI to yield a hexamer. The hexamer is treated with H$_2$, Pd and then subjected to mild acid hydrolysis to remove the benzyl ester and the vinyl ether, respectively. The resulting hexamer is L-G-L-G-L-G.

EXAMPLE 10

Construction of Oligomers

Construction of G-G-L-L-G-G-L-L. Ethyl carboxymethyl acetal is reacted with benzyl glycolate in the presence of dicyclohexylcarbodiimide (DCDI) to yield an acetal benzyl ester dimer. The ester group is removed by treatment with H$_2$, Pd and the dimer is reacted with benzyl lactate in the presence of DCDI. The resulting trimer is treated with H$_2$, Pd and reacted with benzyl lactate in the presence of DCDI to yield a tetramer. The tetramer is treated with H$_2$, Pd and reacted with benzyl glycolate in the presence of DCDI to yield a pentamer. The pentamer is treated with H$_2$, Pd and reacted with benzyl lactate in the presence of DCDI to yield a hexamer. The hexamer is treated with H$_2$, Pd and reacted with benzyl lactate in the presence of DCDI to yield a septimer. The resulting septimer is treated with H$_2$, Pd and reacted with benzyl lactate in the presence of DCDI to yield an octamer. The octamer is treated with H$_2$, Pd and then subjected to mild acid hydrolysis to remove the benzyl ester and the vinyl ether, respectively. The resulting octamer is G-G-L-L-G-G-L-L.

The examples and embodiments depicted in this specification are not intended to be limitations of the invention described herein. Accordingly, one with skill in the art may make modifications in the products and methods of making the products which are intended to be covered by the following claims.

What is claimed is:

1. A process for making a polyester having a predetermined monomeric sequence comprising:
   (i) providing an aliphatic ester of a first hydroxyacid;
   (ii) protecting a hydroxyl group on said aliphatic ester of a first hydroxyacid with a hydroxyl protecting group;
   (iii) subjecting said hydroxyl-protected aliphatic ester of a first hydroxyacid to hydrolysis to remove the aliphatic ester substituent;
   (iv) protecting a carboxyl group on a next hydroxyacid with a carboxyl protecting group;
   (v) reacting said first hydroxyl-protected hydroxyacid with said next carboxyl-protected hydroxyacid; and
   (vi) forming a product having an ester bond between said first hydroxyl-protected hydroxyacid and said next carboxyl-protected hydroxyacid.

2. A process for making a polyester having a predetermined monomeric sequence according to claim 1 further comprising addition of subsequent hydroxyacids by:
   (i) deprotecting said product by removing said carboxyl protecting group to form a free acid;
   (ii) protecting a carboxyl group on a subsequent hydroxyacid with a carboxyl protecting group;
   (iii) reacting said subsequent carboxyl-protected hydroxyacid with said deprotected product;
   (iv) forming an ester bond between said deprotected product and said subsequent carboxyl-protected hydroxyacid; and
   (v) repeating steps (i)-(iv) with additional hydroxyacids until a polymer of desired length is obtained.

3. A process for making a polyester having a predetermined monomeric sequence according to claim 1 further comprising addition of subsequent hydroxyacids by:
   (i) deprotecting said product by removing said hydroxyl-protecting group to form a free alcohol;
   (ii) protecting a hydroxyl group on a subsequent aliphatic ester of a hydroxy acid with a hydroxyl protecting group;
   (iii) subjecting said subsequent aliphatic ester of a hydroxy acid to hydrolysis to remove the aliphatic ester substituent and form a subsequent hydroxyl-protected hydroxyacid;
   (iv) reacting said subsequent hydroxyl-protected hydroxyacid with said deprotected product;
   (v) forming an ester bond between said deprotected product and said subsequent hydroxyl-protected hydroxyacid; and
   (vi) repeating steps (i)-(v) with additional said hydroxyacids until a polymer of desired length is obtained.

4. A process for making a polyester having a predetermined monomeric sequence according to claim 1 wherein said first and next hydroxyacids are selected from the group consisting of $\alpha$-hydroxyacids, $\beta$-hydroxyacids, $\gamma$-hydroxyacids, $\delta$-hydroxyacids and hydroxy polycarboxylic acids.

5. A process for making a polyester having a predetermined monomeric sequence according to claim 4 wherein said first and next hydroxyacids are selected from the group consisting of glycolic acid, lactic acid, hydroxybutyric acid, hydroxyvaleric acid, tartronic acid and citric acid.

6. A process for making a polyester having a predetermined monomeric sequence according to claim 2 wherein said subsequent hydroxyacid is selected from the group consisting of $\alpha$-hydroxyacids, $\beta$-hydroxyacids, $\gamma$-hydroxyacids, $\delta$-hydroxyacids and hydroxy polycarboxylic acids.

7. A process for making a polyester having a predetermined monomeric sequence according to claim 6 wherein said subsequent hydroxyacid is selected from the group consisting of glycolic acid, lactic acid, hydroxybutyric acid, hydroxyvaleric acid, tartronic acid and citric acid.

8. A process for making a polyester having a predetermined monomeric sequence according to claim 3 wherein the hydroxyacid of said subsequent aliphatic ester of a hydroxyacid is selected from the group consisting of $\alpha$-hydroxyacids, $\beta$-hydroxyacids, $\gamma$-hydroxyacids, $\delta$-hydroxyacids and hydroxy polycarboxylic acids.

9. A process for making a polyester having a predetermined monomeric sequence according to claim 8 wherein the hydroxyacid of said subsequent aliphatic ester of a hydroxyacid is selected from the group consisting of glycolic acid, lactic acid, hydroxybutyric acid, hydroxyvaleric acid, tartronic acid and citric acid.

10. A process for making a polyester having a predetermined monomeric sequence according to claim 1 wherein said ester bond is formed in the presence of a dehydrating agent.

11. A process for making a polyester having a predetermined monomeric sequence according to claim 10 wherein said dehydrating agent is selected from the group consisting of dicyclohexylcarbodiimide (DCDI), trifluoroacetic anhydride, and N,N'-carbonyldiimidazole (CDI).

12. A process for making a polyester having a predetermined monomeric sequence according to claim 2 wherein said ester bond is formed in the presence of a dehydrating agent.

13. A process for making a polyester having a predetermined monomeric sequence according to claim 12 wherein said dehydrating agent is selected from the group consisting of dicyclohexylcarbodiimide (DCDI), trifluoroacetic anhydride, and N,N'-carbonyldiimidazole (CDI).

14. A process for making a polyester having a predetermined monomeric sequence according to claim 3 wherein said ester bond is formed in the presence of a dehydrating agent.

15. A process for making a polyester having a predetermined monomeric sequence according to claim 14 wherein said dehydrating agent is selected from the group consisting of dicyclohexylcarbodiimide (DCDI), trifluoroacetic anhydride, and N,N'-carbonyldiimidazole (CDI).

16. A process for making a polyester having a predetermined monomeric sequence according to claim 10 wherein said hydroxyl-protected aliphatic ester of a first hydroxyacid is methoxyethoxymethyl protected ethyl glycolate, said next carboxyl protected hydroxyacid is benzyl lactate and said dehydrating agent is dicyclohexylcarbodiimide.

17. A process for making a polyester having a predetermined monomeric sequence according to claim 1 further comprising
   (i) forming bulk quantities of said product;
   (ii) splitting said bulk quantities into at least first and second portions; removing the hydroxyl protecting group from said first portion to form free alcohols;
   (iv) removing the carboxyl protecting group from said second portion to form free acids;
   (v) combining said free alcohols portion with said free acids portion;
   (vi) reacting said free alcohols portion with said free acids portion in the presence of a dehydrating agent; and
   (vii) forming bulk quantities of a tetramer polyester having a predetermined monomeric sequence.

18. A process for making a polyester having a predetermined monomeric sequence according to claim 17 further comprising continuously repeating steps
   (ii) through
   (vi) with said tetramers from step
   (vii) and further bulk quantities obtained therefrom until a polymer of desired molecular weight is obtained.

19. A process for making a polyester having a predetermined monomeric sequence according to claim 17 further comprising deprotecting said tetramer from step
   (vii) by removing a protecting group selected from the group consisting of hydroxyl protecting groups and carboxyl protecting groups; and adding at least one hydroxyacid selected from the group consisting of hydroxyl-protected hydroxyacids and carboxyl-protected hydroxyacids to said tetramer by ester bond formation to form bulk quantities of an oligomer.

20. A process for making a polyester having a predetermined monomeric sequence according to claim 19 further comprising continuously repeating steps
   (ii) through (vi) with said bulk quantities of said oligomer and further bulk quantities obtained therefrom until a polymer of desired molecular weight is obtained.

21. A process for making a polyester having a predetermined monomeric sequence according to claim 17 wherein first hydroxyl-protected aliphatic ester of a first hydroxyacid is methoxyethoxymethyl protected ethyl glycolate, said next carboxyl protected hydroxyacid is benzyl lactate, said dehydrating agent is dicyclocarbodiimide and said tetramer is MEM-G-L-G-L-Benzyl.

22. A polyester having a predetermined monomeric sequence formed by a process according to claim 1.

23. A polyester having a predetermined monomeric sequence formed by a process according to claim 2.

24. A polyester having a predetermined monomeric sequence formed by a process according to claim 3.

25. A polyester having a predetermined monomeric sequence formed by a process according to claim 16.

26. A polyester having a predetermined monomeric sequence formed by a process according to claim 17.

27. A polyester having a predetermined monomeric sequence formed by a process according to claim 18.

28. A polyester having a predetermined monomeric sequence formed by a process according to claim 20.

29. A medical device comprising a polyester having a predetermined monomeric sequence according to claim 22.

* * * * *